United States Patent [19]

Plate et al.

[11] Patent Number: 5,227,394
[45] Date of Patent: Jul. 13, 1993

[54] PYRAZOLE DERIVATIVES, COMPOSITIONS AND USE

[75] Inventors: Ralf Plate, Oss, Netherlands; Duncan R. Rae, Lanark, Scotland

[73] Assignee: Akzo N.V., Arnhem, Netherlands

[21] Appl. No.: 919,806

[22] Filed: Jul. 27, 1992

[30] Foreign Application Priority Data

Jul. 26, 1991 [EP] European Pat. Off. ...... 91.306.870.6

[51] Int. Cl.$^5$ ............... A61K 31/415; A61K 31/435; C07D 401/04; C07D 487/08
[52] U.S. Cl. .................... 514/406; 514/305; 514/341; 546/133; 546/279; 548/364.7
[58] Field of Search .............. 546/133, 279; 548/364.7; 514/406, 305, 341

[56] References Cited

FOREIGN PATENT DOCUMENTS

| | | |
|---|---|---|
| 0239309 | 9/1987 | European Pat. Off. |
| 0307141 | 3/1989 | European Pat. Off. |
| 0316718 | 5/1989 | European Pat. Off. |
| 0296721 | 4/1990 | European Pat. Off. |
| 0384288 | 8/1990 | European Pat. Off. |
| 0402056 | 12/1990 | European Pat. Off. |
| 0427390 | 5/1991 | European Pat. Off. |

OTHER PUBLICATIONS

M. Ferles et al., "Reaction of a 1-pyridyl-1,3-butanediones and 1,3-dipridyl-1,3-propanediones", Collect. Czech. Chem. Commun., vol. 46, No. 5, pp. 1167-1172, Prague, Czech., (1981).

C. W. Thornber, "Isoterism and Molecular Modification in Drug Design", Chem. Soc. Rev., vol. 18, pp. 563-580, 1979.

Primary Examiner—Robert W. Ramsuer
Attorney, Agent, or Firm—Donna Bobrowicz; William M. Blackstone

[57] ABSTRACT

The invention relates to pyrazole derivative having formula I

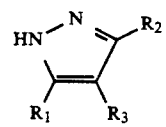

wherein $R_1$ is

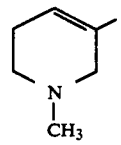

and $R_2$ is hydrogen, or $R_1$ is

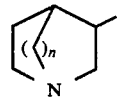

wherein n is 1 or 2 and $R_2$ is hydrogen or halogen; and $R_3$ is bromine or iodine; or a pharmaceutically acceptable salt thereof.

The compounds of this invention have muscarinic properties and can be used for the treatment of cognition disorders, for analgesia, and afore the treatment of cholinergic deficiencies.

12 Claims, No Drawings

PYRAZOLE DERIVATIVES, COMPOSITIONS AND USE

The invention relates to pyrazole derivatives, a process for the preparation thereof, a pharmaceutical composition containing the same, as well as to the use of these pyrazole derivatives for the preparation of a medicament.

The pyrazole derivatives of this invention are novel compounds, but related pyrazole derivatives are known. For instance, 3-(3-methylpyrazol-1-yl)-1-azabicyclo-[2.2.2]octane and 3-(pyrazol-1-yl)-1-azabicyclo[2.2.2]-octane have been described in European Patent Application 427,390 as compounds for the treatment of dementia, and in EP 298,721 1,5-dimethyl-3-(1-methyl-1,2,5,6-tetrahydro-3-pyridyl)pyrazole is disclosed for a similar utility. These known compounds, however, have fairly weak activity as muscarinic cholinergic agonist as indicated by a relatively low oxotremorine binding affinity, or are muscarine antagonists rather than agonists.

The compounds of the present invention have a high binding affinity for the muscarinic cholinergic receptor, as measured by their ability to displace oxotremorine from rat brain membrane homogenate. The high binding affinity is demonstrated by pKi values which are usually higher than 7.

The present invention relates to a pyrazole derivative having formula I

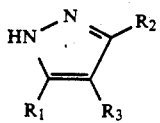

wherein $R_1$ is

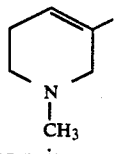

and $R_2$ is hydrogen, or $r_1$ is

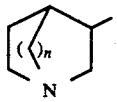

wherein n is 1 or 2 and $R_2$ is hydrogen or halogen; and $R_3$ is bromine or iodine; or a pharmaceutically acceptable salt thereof.

Preferred pyrazole derivatives according to this invention have $R_1$ is 1,2,5,6-tetrahydro-1-methyl-pyridine-3-yl or 1-azabicyclo[2.2.1]heptan-3-yl (n is 1).

The most preferred pyrazole derivative has $R_1$ is 1-aza-bicyclo[2.2.1]heptan-3-yl, $R_2$ is hydrogen, and $R_3$ is bromine or iodine, or a pharmaceutically acceptable salt thereof.

The compounds of this invention have muscarinic properties. They bind preferentially to the agonistic state of the muscarinic cholinergic receptor sites with a 2 to 750 fold preference in comparison with the binding to the antagonistic state of the receptor,. This is exemplified in their ability to displace preferentially the agonist oxotremorine from the binding sites in comparison with their ability to displace the antagonist guinuclidinyl benzilate from the binding sites. Preferred compounds show an agonist/antagonist binding ratio of between 10 and 400. Compounds having ratios very much higher than 750 are undesired, because they may exert side-effects or toxic properties. Compounds having similar pharmacological properties are known, e.g. pilocarpine and oxotremorine, but the chemical structures of these compounds bear no relation to the pyrazole derivatives of this invention.

The pyrazole derivatives are suitable for the treatment of cognition disorders, like presenile and senile dementia, including Alzheimer's disease, for analgesia, and for the treatment of other cholinergic deficiencies, like Huntington's chorea, tardive dyskinesia, hyperkinesia, mania, and Tourette syndrome.

The term halogen used in the definition of formula I means fluorine, chlorine, bromine or iodine. Bromine is the preferred halogen.

The novel compounds of formula I may be isolated from the reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, and ascorbic acid.

The pyrazole derivatives of the invention can be prepared by methods known for the preparation of analogous compounds.

Particular methods of preparation can be advantageous for specific derivatives. For instance, the 1,2,5,6-tetrahydro-1-methylpyridin-3-yl derivatives can easily be prepared from the corresponding pyridinium salts by reduction of the pyridinium ring with suitable reduction means, such as sodium borohydride. The halogen atom(s) can most easily be introduced from the corresponding non-halogenated derivatives by using halogenation agents like N-bromosuccinimide.

Various alternative syntheses are available and well known in the art. Of these various methods a non-limitative number of examples are mentioned, among which the condensation of hydrazine with compounds like $R_1$—CO—$CR_2$=CH—$N(CH_3)_2$, wherein $R_1$ has the previously given meaning, and the condensation of acetylene derivative $R_1$—C≡C—$R_3$ with diazo derivative $R_2$—$CH_2$—N≡N, wherein $R_1$, $R_2$, and $R_3$ have the previously given meanings.

Compounds having $R_1$ is 1-azabicyclo[2.2.2]octan-3-yl or 1-azabicyclo[2.2.]heptan-3-yl can also be prepared by condensation of hydrazine with compounds of the formula $R_1(OH)$—C≡C—CH(O-lower alkyl)$_2$, after which the compound of formula I is obtained by dehydration using dehydration agents normally used for dehydration reactions (for example thionylchloride/benzene), optionally followed by hydrogenation with hydrogen and palladium-carbon or by equivalent methods, and halogenation with halogenation reagents (for example N-bromosuccinimide to obtain bromo derivatives). The term lower alkyl means an alkyl group with preferably 1-4 carbon atoms, like methyl, ethyl, propyl, isopropyl and butyl. Methyl is the preferred lower alkyl group.

The compounds of this invention possess a chiral carbon atom when R1 is 1-azabicyclo[2.2.2]octan-3-yl or 1-aza-bicyclo[2.2.1]heptan-3-yl, and may therefore be obtained as a pure enantiomer, or as a mixture of enantiomers, among which the racemic mixture. Methods for obtaining the pure enantiomers are well known in the art, e.g. synthesis with chiral induction, crystallization of salts which are obtained from optically active acids and the racemic mixture, or chromatography using chiral columns.

The compounds of the invention may be administered enterally or parenterally, and for humans preferably in a daily dosage of 0,001-10 mg per kg body weight. Mixed with pharmaceutically suitable auxiliaries, e.g. as described in the standard reference, Chase et al., Remington's Pharmaceutical Sciences, the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray.

The invention is further illustrated by the following examples.

EXAMPLE 1

3-(4,5-dibromo-1H-ovrazol-3-vl)-1-azabicyclo2.2.21-octane (Z)-2-butenedioate

A suspension of 2.5 g of propargylaldehyde diethylacetal and 2.4 g of potassium t-butoxide in 40 ml of dry tetrahydrofuran was stirred at −10° C. After 1 h a solution of 2.0 g of 3-quinuclidinone in 25 ml of dry tetrahydrofuran was added dropwise. After 2 h stirring at 0° C. an ice water-acetic acid solution was added, and the solvent was removed under reduced pressure. The residue was made alkaline with a 2 N sodium hydroxide solution and the product was extracted with ethyl acetate. After drying over magnesium sulfate and evaporation 4.1 g (84% yield) of 3-(3,3-diethoxy-prop-1-yne)-1-azabicyclo[2.2.2] octan-3-ol was obtained, which, together with 1.85 g of hydrazine dihydrochloride, were dissolved in 50 ml of ethanol and refluxed for 18 h. The solvent was removed under reduced pressure, the residue made alkaline with 2 N sodium hydroxide solution, and the product extracted with ethyl acetate, evaporated to dryness and converted into its hydrochloride by addition of hydrochloric acid in methanol, to give 60% yield of 3-hydroxy-3-(lH-pyrazol-3-yl)-1-azabicyclo[2.2.2]octane. 4.5 g of this compound was suspended in 25 ml of dry benzene, 2 ml of thionylchloride were added and the mixture was heated to reflux. The solvent was removed under reduced pressure, the residue made alkaline with 2 N sodium hydroxide solution, and the product extracted with ethyl acetate and evaporated to dryness to give 63% yield of 3-(lH-pyrazol-3-yl)-1-azabicyclo[2.2.2]oct-2-ene. 1.6 g of this compound was dissolved in 50 ml of methanol and 250 mg of Pd/C were added. The suspension was treated at room temperature with hydrogen at $207.10^3$ Pa in a Parr apparatus. After 24 h 93% of 3-(1H-pyrazol-3-yl)-1-azabicyclo[2.2.2]octan was obtained. To a solution of 0.61 g of this compound in 10 ml of dry dimethylformamide was added under nitrogen at −10° C. a solution of 0.66 g of N-bromosuccinimide in 10 ml of dry dimethylformamide. The mixture was stirred for 3 h, the solution poured into water and extracted with ethyl acetate. The solution was dried over magnesium sulfate, evaporated, and the residue subjected to column chromatography over silica, to give 42% of an oil, which was converted into its maleate by addition of maleic acid. After crystallization from methanol/ethyl acetate 3-(4,5-dibromo-1H-pyrazol-3-yl)-1-azabicyclo[2.2.2]-octane (Z)-2-butenedioate, mp 140° C., was obtained.

EXAMPLE 2

By analogous methods as used in Example 1 were prepared:

3-(4,5-dibromo-1H-pyrazol-3-yl)-1-azabicyclo[2.2.1]-heptane (Z)-2-butenedioate.

3-(4-bromo-1H-pyrazol-3-yl)-azabicyclo[2.2.2]octane (Z)-2-butenedioate. mp 140° C.

3-(5-bromo-4-iodo-lH-pyrazol-3-yl)-1-azabicyclo[2.2.1]-heptane (Z)-2-butenedioate.

3(4-bromo-1H-pyrazol-3-yl)-1-azabicyclo[2.2.1]heptane (Z)-2-butenedioate.

3-(4-iodo-1H-pyrazol-3-yl)-1-azabicyclo[2.2.1]heptane (Z)-2-butenedioate.

EXAMPLE 3

3-(4-bromo-1H-ovrazol-3-vl)-1,2,5,6-tetrahydro-1-methyl-pyridine (E)-2-butenedioate A solution of 125 g of 3-acetylpyridine and 138 g of N,N-dimethylformamide-dimethylacetal in dry dimethyl-formamide was refluxed for 3 h, after which the solution was evaporated to dryness and the product triturated with ether to give N,N-dimethyl-3-oxo-3-(3-pyridinyl)-prop-1-enamine in 72% yield. To a solution of 10.2 g of this product in 2-methoxyethanol 3.2 g of hydrazine were added under nitrogen and the mixture was heated. After 2 h the solvent was removed in vacuo to give quantitatively 3-(lH-pyrazol-3-yl)pyridine, which was dissolved in dimethylformamide. To this solution 22.8 g of N-bromosuccinimide were added in small portions over a period of 30 min, maintaining the temperature at 0°–5° C. The mixture was stirred for 3 h, poured into water, extracted with ethyl acetate, dried over sodium sulfate and evaporated to dryness, to obtain crude 3-(4-bromo-1H-pyrazol-3-yl)pyridine. To a solution of 13.5 g of this product in 190 ml of acetonitrile were added 17.5 g of methyl iodide under nitrogen, after which the solution was refluxed for 3 h. After cooling the crystalline material was filtered to give 3-(4-bromo-1H-pyrazol-3-yl)-1-methylpyridinium iodide in 71% yield. 15.6 g of this product was suspended in methanol and 5.7 g of sodium borohydride were added in small portions over 20 min at 0° C. After 1 h of stirring glacial acetic acid was added and the pH was adjusted to 6. The solvent was removed in vacuo, the residue suspended in brine and basified, and the product extracted with ethyl acetate. After drying over sodium sulfate and evaporation to dryness 3-(4-bromo-1H-pyrazol-3-yl)-1,2,5,6-tetrahydro-1-methylpyridine was obtained in 93% yield, and converted into its fumaric salt, which was recrystallized from methanol to give 3-(4-bromo-1H-pyrazol-3-yl)-1,2,5,6-tetrahydro-1-methylpyridine (E)-2-butenedioate. mp 228° C.

EXAMPLE 4

By analogous methods as used in Example 3 were prepared:

3-(4,5-dibromo-1H-pyrazol-3-yl)-1,2,5,6-tetrahydro-1-methylpyridine (Z)-2-butenedioate. mp 208° C.

1,2,5,6-tetrahydro-3-(5-bromo-4-iodo-1H-pyrazol-3-yl)-1-methylpyridine (Z)-2-butenedioate. mp 132° C.

1,2,5,6-tetrahydro-3-(4-iodo-1H-pyrazol-3-yl)-1-methyl-yl-pyridine (Z)-2-butenedioate. mp 178° C.

We claim:

1. A pyrazole derivative having the formula

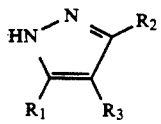
(I)

wherein $R_1$ is

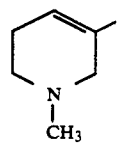

and $R_2$ is hydrogen, or $R_1$ is

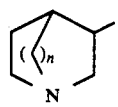

wherein n is 1 or 2, and $R_2$ is hydrogen or halogen; and $R_3$ is bromine or iodine; or a pharmaceutically acceptable salt thereof.

2. The pyrazole derivative of claim 1, wherein $R_1$ is 1,2,5,6-tetrahydro-1-methylpyridin-b 3-yl or 1-azabicyclo heptan-3-yl.

3. The pyrazole derivative of claim 1, wherein $R_1$ is 1-azabicyclo heptan-3-yl, $R_2$ is hydrogen.

4. A pharmaceutical composition comprising the pyrazole derivative of claim 1 in admixture with pharmaceutically acceptable auxiliaries.

5. A pharmaceutical composition comprising the pyrazole derivative of claim 2 in admixture with pharmaceutically acceptable auxiliaries.

6. A pharmaceutical composition comprising the pyrazole derivative of claim 3 in admixture with pharmaceutically acceptable auxiliaries.

7. A method of treating cognition disorders and cholinergic deficiencies in a subject comprising administering therapeutically effective amounts of the pyrazole derivative according to claim 1 to said subject.

8. A method of treating cognition disorders and cholinergic deficiencies in a subject comprising administering therapeutically effective amounts of the pyrazole derivative according to claim 2 to said subject.

9. A method of treating cognition disorders and cholinergic deficiencies in a subject comprising administering therapeutically effective amounts of the pyrazole derivative according to claim 3 to said subject.

10. A method of inducing analgesia in a subject comprising administering therapeutically effective amounts of the pyrazole derivative according to claim 1 to said subject.

11. A method of inducing analgesia in a subject comprising administering therapeutically effective amounts of the pyrazole derivative according to claim 2 to said subject.

12. A method of inducing analgesia in a subject comprising administering therapeutically effective amounts of the pyrazole derivative according to claim 3 to said subject.

* * * * *